*(12)* United States Patent
Berthiaume et al.

(10) Patent No.: US 8,002,763 B2
(45) Date of Patent: Aug. 23, 2011

(54) CATHETER FLUSHING MANDREL

(75) Inventors: William Berthiaume, Santa Rosa, CA (US); Don Tran, Novato, CA (US); Chris Collins, San Rafael, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 12/862,505

(22) Filed: Aug. 24, 2010

(65) Prior Publication Data
US 2010/0324537 A1 Dec. 23, 2010

Related U.S. Application Data

(62) Division of application No. 12/109,265, filed on Apr. 24, 2008, now abandoned.

(51) Int. Cl.
*A61M 31/00* (2006.01)
*A61M 25/00* (2006.01)
*A61M 29/00* (2006.01)
*A61B 5/00* (2006.01)
(52) U.S. Cl. ......... 604/500; 604/523; 600/585; 606/191
(58) Field of Classification Search ............... 604/96.01, 604/280, 500, 523; 600/585; 606/191–195
See application file for complete search history.

(56) References Cited

U.S. PATENT DOCUMENTS

| 3,528,406 | A | | 9/1970 | Jeckel et al. |
| 3,863,641 | A | * | 2/1975 | Popa ............................. 604/267 |
| 5,100,385 | A | | 3/1992 | Bromander |
| 5,256,144 | A | | 10/1993 | Kraus et al. |
| 5,334,147 | A | * | 8/1994 | Johnson ................... 604/103.04 |
| 5,545,138 | A | * | 8/1996 | Fugoso et al. ............. 604/103.1 |
| 5,733,248 | A | * | 3/1998 | Adams et al. ................. 600/585 |
| 6,610,068 | B1 | | 8/2003 | Yang |
| 6,733,473 | B1 | | 5/2004 | Reifart et al. |
| 2003/0208222 | A1 | | 11/2003 | Zadno-Azizi |
| 2004/0059244 | A1 | | 3/2004 | Flores et al. |
| 2010/0125324 | A1 | * | 5/2010 | Collins et al. ................ 623/1.11 |

* cited by examiner

*Primary Examiner* — Theodore J Stigell
*Assistant Examiner* — William Carpenter

(57) ABSTRACT

A mandrel includes a mandrel body with a proximal major diameter barrel section, a diameter reducing/tapered portion and a distal minor diameter barrel section. The tapered portion connects the proximal major diameter barrel section and distal minor diameter barrel section. The proximal major diameter barrel section has a major diameter, the distal minor diameter barrel section has a minor diameter, the minor diameter less than the major diameter. The minor diameter is less than a diameter of an inner lumen of a coaxial catheter, and the major diameter exceeds the inner diameter of the outer lumen guidewire exit port of the coaxial catheter, and the tapered portion is sized to form a fluid seal the inner diameter of the outer lumen guidewire exit port. The distal minor diameter barrel section of the mandrel occupies and substantially seals and prevent flow through it to the catheter distal end guidewire entry port.

5 Claims, 4 Drawing Sheets

200

200

300

_US 8,002,763 B2_

CATHETER FLUSHING MANDREL

RELATED APPLICATIONS

This application is a Division of and claims the benefit of U.S. patent application Ser. No. 12/109,265 filed Apr. 24, 2008. The disclosures of which are herein incorporated by reference in their entirety.

TECHNICAL FIELD

The technical field of this disclosure is medical devices, particularly, a catheter flushing mandrel.

BACKGROUND

Catheters are used in a number of medical procedures to deliver medical devices to a target site within a body and other purposes. Catheters, typically, define an inner lumen with an inner wall of the catheter, and this inner lumen can be divided into dedicated lumens for a number of purposes, such as holding contrast fluids, delivering devices, or the like. Prior to insertion into the body, catheters must be flushed with a fluid, often saline.

In a coaxial catheter, flushing can be difficult and time consuming, as two separate connections must be made to flush the inner lumen and outer lumen. This requires not only extra time in the surgical suite, but also mandates additional handling. Additionally, at times medical professionals create a physical seal for the flushing operation using their fingers, which is undesirable.

It would be desirable to overcome the above disadvantages.

SUMMARY OF THE INVENTION

One aspect according to the present invention provides a mandrel that includes a mandrel body with a proximal major diameter barrel section, a diameter reducing portion, such as a tapered or step down (shoulder) portion and a distal minor diameter barrel section. The tapered portion connects the proximal major diameter barrel section and distal minor diameter barrel section. The proximal major diameter barrel section has a major diameter, the distal minor diameter barrel section has a minor diameter, the minor diameter less than the major diameter. The minor diameter is less than a diameter of an inner lumen of a coaxial catheter, and the major diameter exceeds an inner diameter of a guidewire exit port on the outer lumen of the coaxial catheter, and the tapered portion is sized to form a fluid seal with the guidewire exit port on the outer lumen of the coaxial catheter.

Another aspect according to the invention provides a catheter system including a coaxial catheter. The coaxial catheter includes an inner lumen member defining an inner lumen and an outer lumen member defining an outer lumen. Additionally, the system includes a mandrel that includes a mandrel body with a proximal major diameter barrel section, a tapered portion and a distal minor diameter barrel section. The tapered portion connects the proximal major diameter barrel section and distal minor diameter barrel section. The proximal major diameter barrel section has a major diameter, the distal minor diameter barrel section has a minor diameter, the minor diameter less than the major diameter. The minor diameter is less than a diameter of an inner lumen of a coaxial catheter, and the major diameter exceeds an inner diameter of a guidewire exit port on the outer lumen of the coaxial catheter, and the tapered portion is sized to form a fluid seal with the guidewire exit port on the outer lumen of the coaxial catheter.

Another aspect according to the invention provides a method of flushing a catheter. The method includes providing a coaxial catheter, the coaxial catheter including an inner lumen and an outer lumen, and inserting a flushing mandrel into the inner lumen. The method further includes forming a fluid seal between the flushing mandrel and the wall defining the inner diameter of the outer lumen guidewire exit port based on the insertion, flushing the outer lumen based on the formed seal, and breaking the fluid seal after the flushing by removal of the flushing mandrel entirely from the coaxial catheter. Further, the method includes flushing the inner lumen based on the broken seal and removal of the flushing mandrel based on the flushing of the outer lumen.

The foregoing and other features and advantages will become further apparent from the following detailed description, read in conjunction with the accompanying drawings. The detailed description and drawings are merely illustrative.

DETAILED DESCRIPTION

Embodiments according to the invention will now be described by reference to the figures wherein like numbers refer to like structures. The terms "distal" and "proximal" are used herein with reference to the treating clinician during the use of the catheter system: "distal" indicates delivery system portion distant from, or a direction away from the clinician and "proximal" indicates an apparatus portion near to, or a direction towards the clinician.

Figure 1:
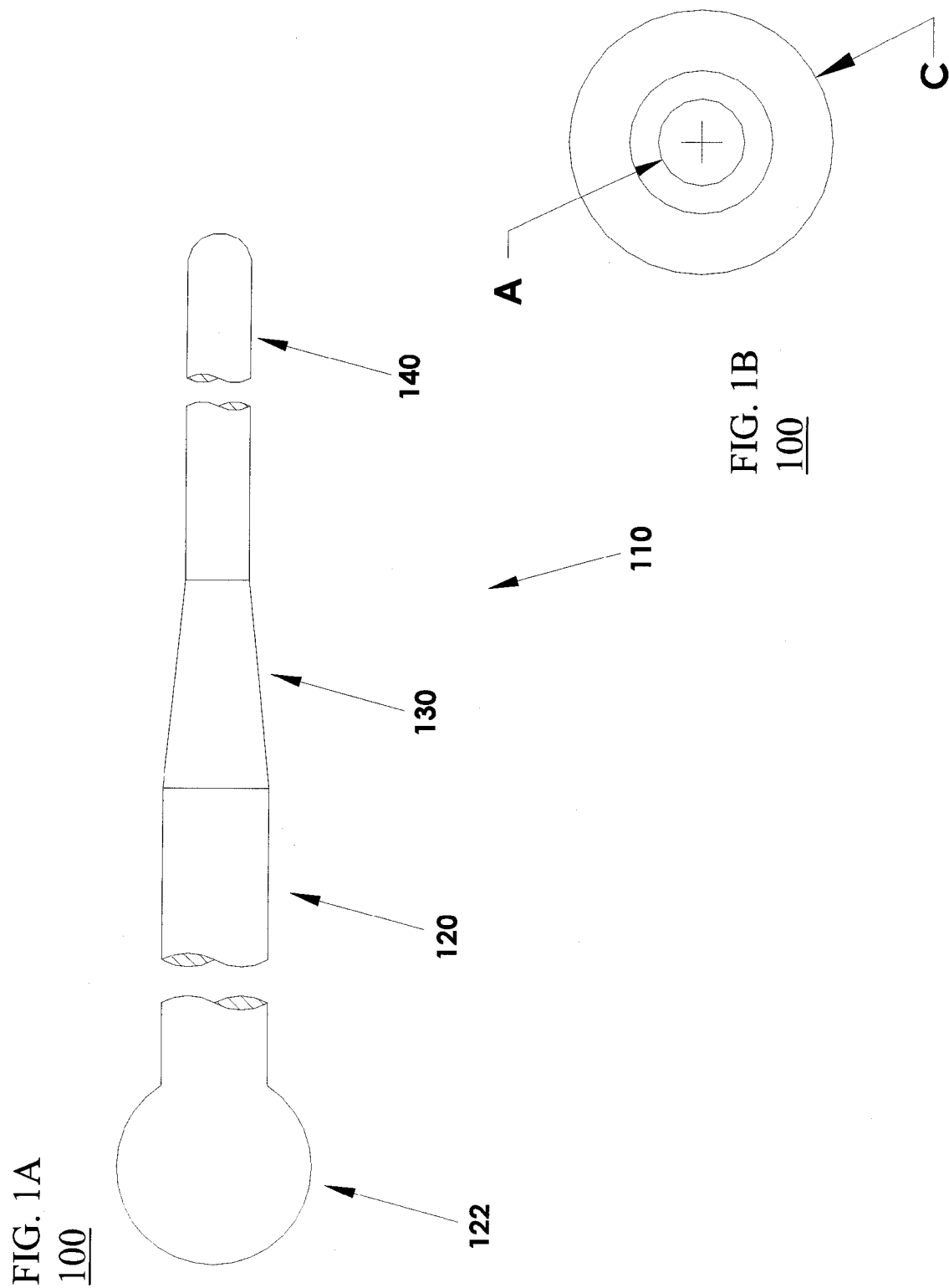
FIG. 1A is a side view of a mandrel.
FIG. 1B is an end view of a mandrel.
Figure 2:
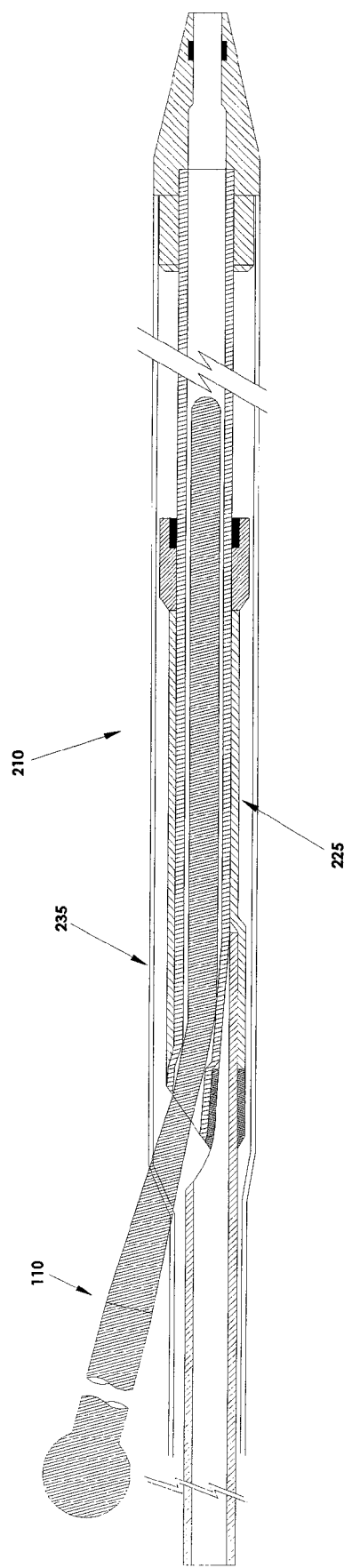
FIG. 2 is a cross sectional view of a catheter system.

FIGS. 1A and 1B illustrate one embodiment of a mandrel 100. Mandrel 100 includes a mandrel body 110 including a proximal major diameter barrel section 120, a tapered portion 130 (a diameter reducing section, e.g., a step down portion or a shoulder), and a distal minor diameter barrel section 140. Tapered portion 130 connects the proximal major diameter barrel section 120 to the distal minor diameter barrel section 140. The proximal major diameter barrel section 120 has a major diameter C and the distal minor diameter barrel section 140 has a minor diameter A. Minor diameter A is less than the major diameter C. Minor diameter A is less than a diameter of an inner lumen 225 (FIG. 2) of a coaxial cavity (such as self expanding device (stent) or drug shielding space or covering) delivery catheter 210 (FIG. 2), and the major diameter A exceeds an inner diameter of a guidewire exit port located on the outer lumen 235 (FIG. 2) of the coaxial catheter 210 (FIG. 2). In one embodiment, C is 0.019 inches. In one embodiment, A is 0.015 inches. In one embodiment, the mandrel overall length is approximately 15". In one embodiment, the proximal major diameter barrel section 120 is approximately 5.5 inches long. In one embodiment, the distal minor diameter barrel section 140 is approximately 8.5 inches long. (while shown in the figures as terminating within the catheter, the mandrel would preferably be long enough to extend through and exit the distal end of the catheter as it acts as a substantial seal of the guidewire lumen). In one embodiment, tapered section 130 is approximately 1" long. In one embodiment, the proximal major diameter barrel section 120 includes a ball 122 of approximately 0.035" diameter. Tapered portion 130 is sized to form a fluid seal with a guidewire exit port of an outer lumen 235 (FIG. 2) of the sheath of the coaxial catheter 210 (FIG. 2). The coaxial catheter is a self expanding device delivery rapid exchange catheter. While illustrated in FIG. 1 as substantially linear, any number of shapes, including arcuate shapes, can be used for the mandrel.

FIG. 2 illustrates a catheter coaxial element delivery system 200. Catheter system 200 includes a coaxial catheter 210 including an inner lumen 225 and an outer lumen 235. Additionally, catheter system 200 includes a mandrel 100, as described in FIG. 1. The device to be delivered contained within the outer sheath and outside the inner shaft enclosing the guidewire lumen is not shown, but a stent stop element part of the delivery system for a self expanding stent is shown (without the stent). Persons skilled in the art are familiar with the configuration.

Figure 3:
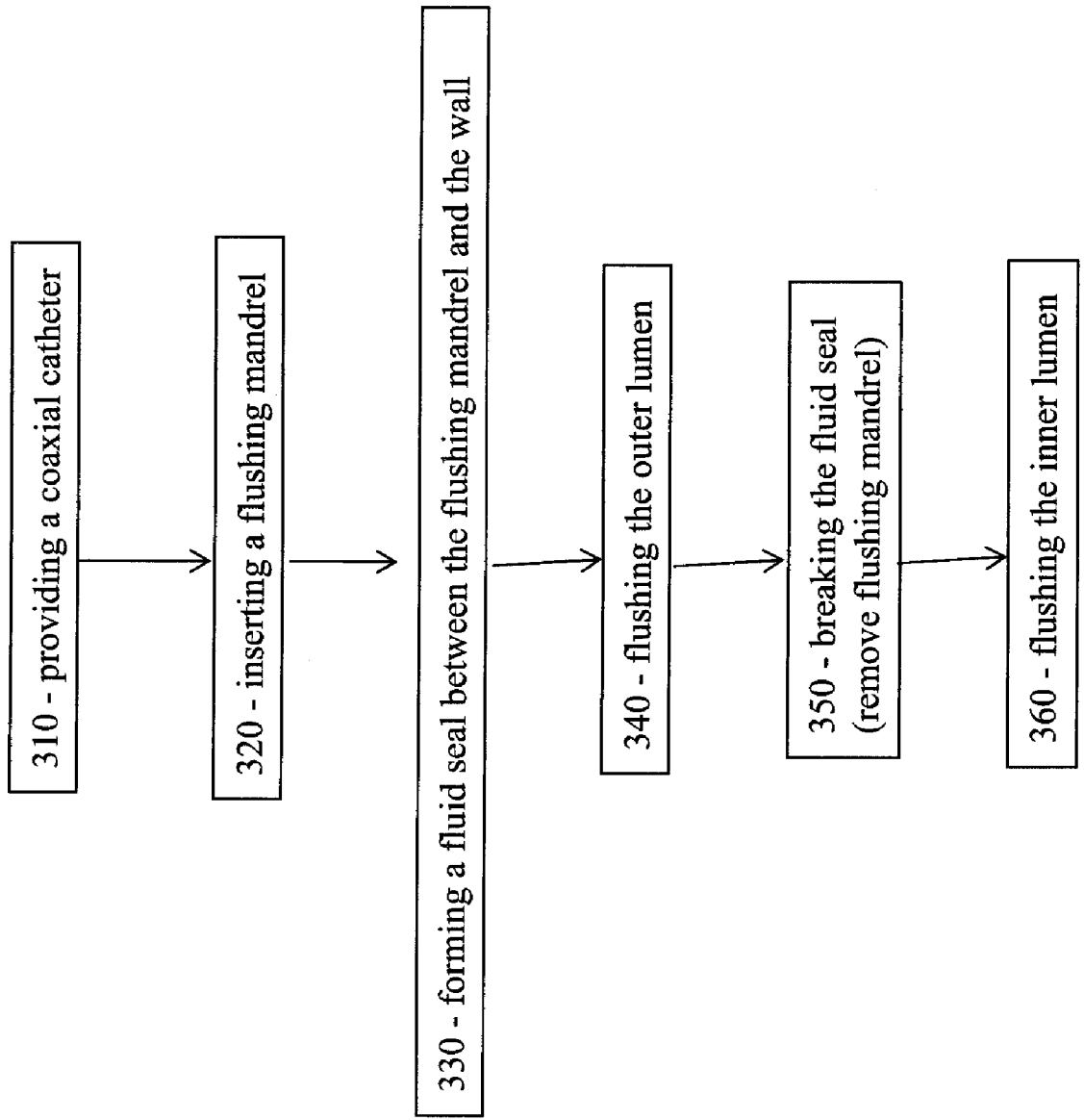
FIG. 3 is a flowchart of the steps of a method of flushing a catheter.

FIG. 3 illustrates a flowchart of a method 300 for flushing a catheter. Method 300 begins at step 310 by providing a coaxial catheter, the coaxial catheter including an inner lumen and an outer lumen, with an internal guidewire exit of the inner lumen communicating to an external guidewire exit port on the outer lumen. At step 320, a flushing mandrel, such as mandrel 100 is inserted into the inner lumen via (and through) the outer lumen guide wire exit port, forming a fluid seal with the outer lumen guidewire exit port. The flushing mandrel is inserted into the inner lumen by advancing the mandrel into the inner lumen until a taper (or other diameter reducing portion or step down or shoulder) on the mandrel contacts the wall defining the inner diameter of the outer lumen guidewire exit port. In one example, the catheter is a self expanding rapid exchange catheter, and the mandrel is inserted into the proximal guidewire exit ports of the sheath and inner member.

At step 330, a fluid seal is formed between the flushing mandrel and the wall defining the inner diameter of the outer lumen guidewire exit port based on the insertion. Once the fluid seal is formed, the outer lumen is flushed by introducing a flushing fluid, such as saline, around the mandrel, and into the outer lumen at step 340. In one embodiment, a syringe is connected to a volume of flushing fluid, and the flushing fluid is introduced into the outer lumen via the syringe. Alternatively, a luer connector or stylet may be used to introduce the flushing fluid. As the fluid enters the outer lumen, any air within the lumen is expelled.

Figure 4:
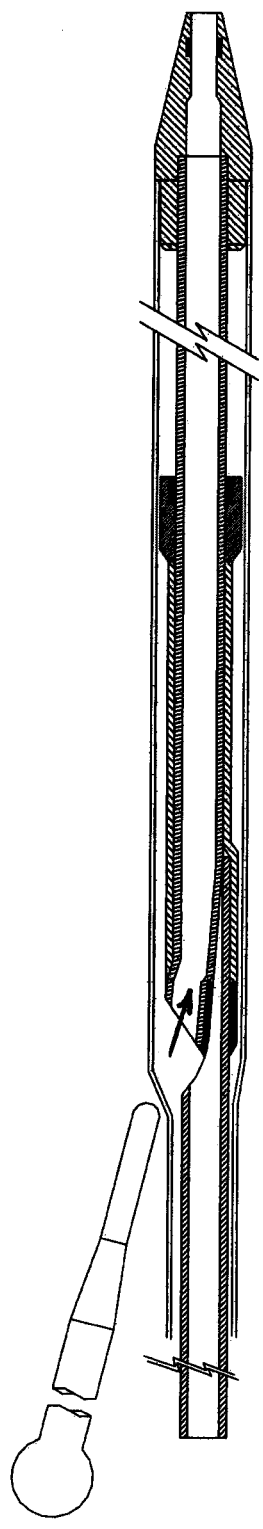
FIGS. 4, 5, and 6 illustrate the use of the mandrel and fluid flow in a catheter system.

Once the outer lumen has been flushed, the fluid seal is broken at step 350. The fluid seal is broken by removal of the flushing mandrel from the coaxial catheter. The mandrel may then be disposed of in any appropriate manner. After the fluid seal has been broken, the inner lumen is flushed at step 360. In one embodiment, the inner lumen is flushed by introducing additional volumes of the flushing fluid. FIG. 4 illustrates a mandrel in the process of being inserted into a coaxial sheath equipped device delivery RX catheter.

Figure 5:
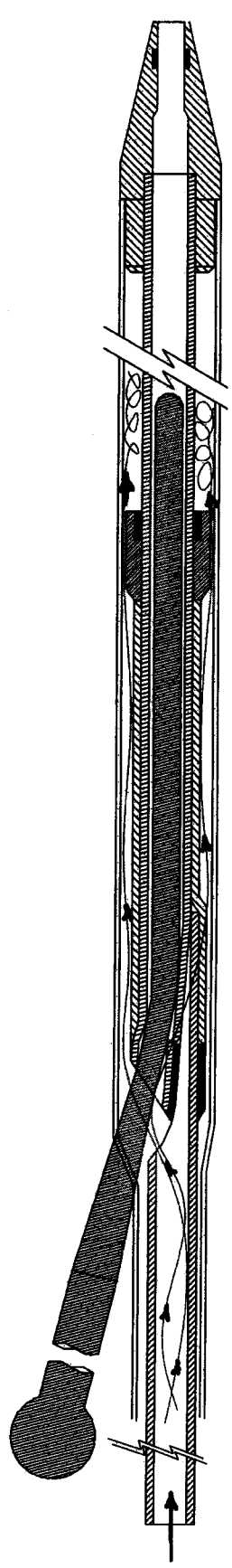

In FIG. 5, a fluid seal has been formed between the mandrel and the sheath such that the smaller portion of the mandrel substantially occupies the guidewire lumen extending proximally from the guidewire exit port. Flushing fluid flow from the proximal portion of the catheter is initiated (indicated with arrows on a continuous line indicating the direction and path of fluid flow). The mandrel blocks fluid flow into the guidewire lumen and causes flushing fluid flow into the outer lumen, flushing the outer lumen (and for example a self expanding stent or drug coating disposed in this outer lumen space.

Figure 6:
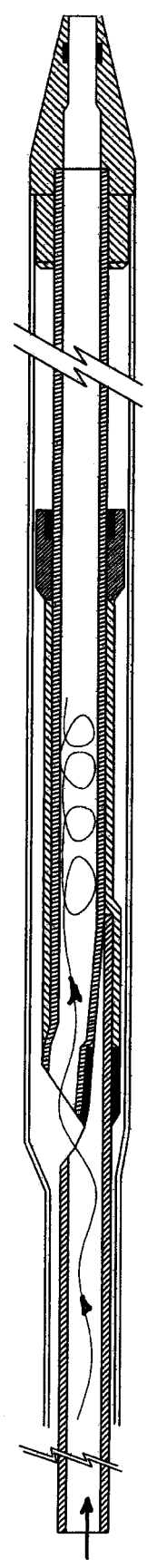

In FIG. 6, the mandrel has been removed while the flushing fluid flow continues, and the fluid is now flowing (as indicated by the arrows) into the inner (guidewire) lumen, flushing the inner lumen. The catheter is now fully flushed and ready for use.

In one embodiment, the flushing mandrel is placed into the coaxial catheter prior to shipping, providing additional support for the end of the catheter during shipping, and prior to use in a clinical procedure.

The mandrel may be manufactured from any appropriate material, but stainless steel is currently preferred. Other biocompatible materials or other easily sterilized materials may also be used.

While specific embodiments of the invention are disclosed herein, various changes and modifications can be made without departing from the spirit and scope of the invention.

The invention claimed is:

1. A method of flushing a catheter, the method comprising:
providing a coaxial catheter, the coaxial catheter including an inner lumen and an outer lumen;
inserting a flushing mandrel into the inner lumen;
forming a fluid seal between the flushing mandrel and a wall defining the inner diameter of a outer lumen guidewire exit port based on the insertion;
flushing the outer lumen based on the formed seal;
breaking the fluid seal after the flushing;
removing the flushing mandrel based on the flushing of the inner lumen; and
flushing the inner lumen based on the broken seal.

2. The method of claim 1 wherein the flushing mandrel comprises a mandrel body including a proximal major diameter barrel section, a tapered portion and a distal minor diameter barrel section, the tapered portion connecting the proximal major diameter barrel section to the distal minor diameter barrel section, and wherein the proximal major diameter barrel section has a major diameter, the distal minor diameter barrel section has a minor diameter, the minor diameter less than the major diameter; and wherein the minor diameter is less than a diameter of the inner mandrel lumen, and wherein the major diameter exceeds a diameter of the inner diameter of the outer lumen guidewire exit port, and wherein the tapered portion is sized to form a fluid seal with the outer lumen guidewire exit port.

3. The method of claim 2 wherein inserting a flushing mandrel into the inner lumen via (and through) the guidewire exit port on the outer lumen comprises advancing the mandrel into the inner lumen until a taper on the mandrel contacts the wall defining the inner diameter of the outer lumen guidewire exit port.

4. The method of claim 1 wherein inserting a flushing mandrel into the inner lumen comprises advancing the mandrel into the inner lumen via (and through) the guidewire exit port on the outer lumen until a taper on the flushing mandrel contacts the wall defining the inner diameter of the outer lumen guidewire exit port.

5. The method of claim 4 wherein breaking the fluid seal comprises removing the flushing mandrel entirely from the coaxial catheter in an axial direction.

* * * * *

UNITED STATES PATENT AND TRADEMARK OFFICE
CERTIFICATE OF CORRECTION

| | | |
|---|---|---|
| PATENT NO. | : 8,002,763 B2 | Page 1 of 1 |
| APPLICATION NO. | : 12/862505 | |
| DATED | : August 23, 2011 | |
| INVENTOR(S) | : William Berthiaume et al. | |

It is certified that error appears in the above-identified patent and that said Letters Patent is hereby corrected as shown below:

Column 4, line 27, "of a outer" should be changed to --of the outer--

Signed and Sealed this
Twenty-ninth Day of November, 2011

David J. Kappos
*Director of the United States Patent and Trademark Office*